United States Patent [19]
Liang

[11] Patent Number: 5,986,141
[45] Date of Patent: Nov. 16, 1999

[54] PROCESS FOR THE PRODUCTION OF CYCLOPROPANEMETHYLAMINE

[75] Inventor: Shaowo Liang, Kingsport, Tenn.

[73] Assignee: Eastman Chemical Company, Kingsport, Tenn.

[21] Appl. No.: 09/162,570

[22] Filed: Sep. 29, 1998

[51] Int. Cl.$^6$ .................................................. C07C 85/08
[52] U.S. Cl. ............................................................ 564/446
[58] Field of Search .............................................. 564/446

[56] References Cited

U.S. PATENT DOCUMENTS

| | | |
|---|---|---|
| 2,556,325 | 6/1951 | Fluchaire et al. . |
| 3,830,810 | 8/1974 | Berre et al. . |
| 3,847,985 | 11/1974 | Linder et al. . |
| 4,275,238 | 6/1981 | Petree et al. . |
| 4,568,669 | 2/1986 | Bijrtinghaus et al. . |
| 5,082,956 | 1/1992 | Monnier et al. . |
| 5,117,012 | 5/1992 | Stavinoha et al. . |
| 5,254,701 | 10/1993 | Falling et al. . |
| 5,312,931 | 5/1994 | Stavinoha . |
| 5,315,019 | 5/1994 | Phillips et al. . |
| 5,362,890 | 11/1994 | Stavinoha et al. . |
| 5,502,257 | 3/1996 | Liang et al. . |
| 5,536,851 | 7/1996 | Monnier . |
| 5,670,672 | 9/1997 | Monnier et al. . |
| 5,681,969 | 10/1997 | Nolen et al. . |
| 5,834,490 | 11/1998 | Verde-Casanova et al. . |

FOREIGN PATENT DOCUMENTS

| | | |
|---|---|---|
| WO9407896 | 4/1994 | WIPO . |
| WO 9506630 | 3/1995 | WIPO . |
| WO9512576 | 5/1995 | WIPO . |

OTHER PUBLICATIONS

Izv. Akad. Nauk SSSR. Ser. Khim., 12, 2878, (1987).

*Primary Examiner*—Samuel Barts
*Attorney, Agent, or Firm*—Michael J. Blake; Harry J. Gwinnell

[57] ABSTRACT

Disclosed is a process for the preparation of cyclopropanemethylamine (CPMA) from cyclopropanecarboxaldehyde (CPCA), ammonia and hydrogen by a two-step process wherein CPCA is contacted with ammonia to form an imine followed by the hydrogenation of the imine in the presence of a nickel or cobalt catalyst to obtain CPMA in high yields and high selectivity.

5 Claims, No Drawings

PROCESS FOR THE PRODUCTION OF CYCLOPROPANEMETHYLAMINE

The present invention pertains to a process for the production of cyclopropanemethylamine (CPMA) from cyclopropanecarboxaldehyde (CPCA), ammonia and hydrogen. More specifically, this invention pertains to the preparation of CPMA by a two-step process wherein CPCA is contacted with ammonia to form an imine followed by the hydrogenation of the imine in the presence of a nickel or cobalt catalyst to obtain CPMA in high yields and high selectivity.

The preparation of CPMA by catalytic cyclopropanation of allylamine with diazomethane is described in *Izv. Akad. Nauk SSSR, Ser. Khim.,* 12, 2878, (1987). The disclosed method requires the use of highly toxic and explosive materials such as diazomethane which presents severe safety problems for commercial-scale production of CPMA. German Patent DE 2061035 describes a process for preparing CPMA by hydrogenating cyanocyclopropane in the presence of Raney nickel. The cyanocyclopropane employed is a relatively expensive reactant.

U.S. Pat. No. 4,275,238 describes the preparation of N-propyl-cyclopropylmethylamine by reductive alkylation utilizing propylamine and CPCA. The '238 patent discloses the reaction of propylamine with CPCA to form an imine compound which then is reduced to form the final product. The two reactions involved in the process preferably are performed simultaneously in situ under hydrogen pressure. This patent identifies 5% platinum on carbon as being a suitable catalyst and indicates that borohydride and nickel reducing catalysts are not suitable for the simultaneous reaction process. The reductive alkylation process described in the '238 patent also requires a careful and slow addition of CPCA into a pressurized system containing platinum catalyst and n-propylamine in order to maintain constant temperature and pressure.

The process of the present invention provides an economical and simple means for the production of CPMA, which avoids the necessity of using expensive reagents, handling unsafe reagents, and the difficulty of process controls. In accordance with the present invention, CPMA is produced by a process comprising (1) contacting CPCA with ammonia in a reaction zone to produce an imine compound having the structure CP—CH=NH wherein CP is cyclopropyl and (2) contacting the imine compound with hydrogen at a temperature of about 10 to 150° C. and a hydrogen pressure of about 1 to 415 bar absolute (bara) in the presence of a nickel or cobalt catalyst. The process typically provides a selectivity of CPCA to CPMA in the range of 92 to 98% when the overall conversion of CPCA to other compounds is in the 98 to 100% range. Advantages of the two-step process of the present invention include the elimination or substantial minimization of side reactions which result in the opening of the cyclopropane ring and in the formation of cyclopropanemethanol due to hydrogenation of the aldehyde group of the CPCA reactant. Cyclopropanemethylamine is a valuable intermediate for the synthesis of pharmaceuticals and agrochemicals See, for example, PCT Patent Application WO 9506630, PCT Patent Application WO 9512576, PCT Patent Application WO 9407896, German Patent DE 3236431 and German Patent DE 2258243). The first step of the process is carried out at a temperature in the range of about −5 to 150° C., preferably about 20 to 50° C., and in the substantial absence of the combination of a hydrogenation catalyst and hydrogen to form the imine compound. Although a solvent or diluent such as water and/or methanol may be present during the first step of the process, the use of such an extraneous solvent or diluent is neither necessary nor preferred. The ammonia reactant employed in the process of this invention can be in the form of a gas, a liquid, a gas/liquid mixture or aqueous ammonia solution. The amounts of ammonia and CPCA charged or fed to the reaction zone will give an ammonia:CPCA mole ratio in the range of 1:1 to 100:1, preferably 2:1 to 6:1 and most preferably 3:1 to 4:1. The excess ammonia can effectively reduce the formation of secondary and/or tertiary amine to trace quantities. The process preferably is carried out in a pressure vessel using essentially undiluted, i.e., substantially pure, e.g., having a purity of at least 98%, ammonia and in the absence of an added solvent which has significant advantages in production rate of the process and in simplicity of product isolation. The first step of the process preferably is carried out using essentially pure, i.e., undiluted, ammonia at a pressure in the range of ambient to 100 bara. It is possible although not preferred to use organic amines, e.g., primary and secondary amines, in the process of this invention to produce alkylated aminomethylcyclopropanes. The first step is carried out over a period of time during which at least 85%, preferably at least 95% of the CPCA reactant has been converted to other compounds, primarily to the imine compound. The hydrogenation catalyst utilized in the second step may be present, and as a matter of convenience preferably is present, during the first step of the process.

In the second step of the process of my invention, the imine compound formed in step (1) is contacted with hydrogen at a temperature of about 10 to 150° C. and a hydrogen pressure of about 1 to 415 bar absolute (bara) in the presence of a nickel or cobalt catalyst. Like the operation of step (1), the use of an extraneous solvent such as methanol and/or water is permissible but not preferred. The second step preferably is carried out at a temperature in the range of about 20 to 80° C. and a total pressure in the range of about 1.4 to 70 bara. The optimum combination of temperature may depend on factors such as the contact time of the imine with the hydrogenation catalyst, the amount of catalyst and/or the particular catalyst used and other process variables.

Examples of the nickel and cobalt catalysts which may be employed in the second step of the process of this invention include Raney nickel, Raney cobalt and supported nickel and cobalt catalysts. The support materials of the supported nickel and supported cobalt catalysts may be selected from a wide variety of known catalyst support materials such as, for example, carbon, alumina, silica, silica-alumina, titania, kieselguhr, molecular sieves, zeolites, and the like. The nickel or cobalt catalysts may contain minor amounts of modifiers and or promoters such as, for example, molybdenum, chromium, iron, zirconium and cobalt or nickel. The supported nickel or cobalt catalyst comprise from 20–70, preferably from 40 to 60 weight percent nickel or cobalt. Raney nickel, Raney cobalt and 40–60 weight percent nickel on alumina constitute the preferred hydrogenation catalysts. The amount of catalyst used in the second step is any amount which will effect hydrogenation of the imine to CPMA. For example, in batch operation using Raney nickel, the amount of catalyst utilized typically is in the range of 0.05 to 50 weight percent based on the weight of the CPCA reactant. However, the catalyst concentration cannot be specified when the process is operated in a continuous fashion employing a fixed bed of a supported nickel or cobalt catalyst.

High purity of CPCA is not required for the process of the present invention. For example, CPCA containing 5 to 15 weight percent crotonaldehyde typically is obtained in the preparation of CPCA by the thermal isomerization of 2,3-dihydrofuran. When such CPCA/crotonaldehyde mixtures are utilized in the present process, the crotonaldehyde reacts with ammonia to produce high-boiling materials which may be removed readily from the CPMA product by distillation. In addition, the crotonaldehyde has no adverse effect on the catalyst with the regard to catalyst life or selectivity. One or both steps of the process may be carried out in the presence of an inert solvent. Examples of such solvents include water, aliphatic and aromatic hydrocarbons such as cyclohexane, heptane, toluene, xylene, mix xylenes and the like, ethers such as tetrahydrofuran, alcohols such as methanol and ethanol. It is preferred, however, to operate the process in the absence, or substantial absence, of any extraneous solvent.

The CPCA utilized in the present invention is readily produced by the thermal isomerization of 2,3-dihydrofuran (2,3-DHF) according to the process described in U.S. Pat. No. 5,502,257. 2,3-DHF may be obtained by the isomerization of 2,5-DHF according to the processes described in U.S. Pat. Nos. 2,556,325, 5,254,701, 5,536,851, 5,670,672, and 5,681,969. 2,5-DHF may be obtained from 1,3-butadiene by the steps of (1) partially oxidizing butadiene to 3,4-epoxy-1-butene and (2) isomerizing the 3,4-epoxy-1-butene to 2,5-DHF. The selective oxidation of butadiene to 3,4-epoxy-1-butene may be accomplished by the processes described in U.S. Pat. Nos. 5,117,012, 5,312,931 and 5,362,890. The isomerization of 3,4-epoxy-1-butene to 2,5-DHF may be carried out according to the processes disclosed in U.S. Pat. Nos. 5,082,956 and 5,315,019.

A particularly preferred embodiment of the process of this invention involves the use of a single pressure vessel. This embodiment is a process for the preparation of CPMA in a single pressure vessel by the steps consisting essentially of (1) contacting CPCA with ammonia at a temperature of 20–50° C. and a total pressure of ambient to about 22 bara in the pressure vessel using an ammonia:CPCA mole ratio of about 3:1 to 4:1 to produce an imine having the formula CP—CH=NH wherein CP is cyclopropyl and (2) contacting the reaction mixture resulting from step (1) with hydrogen at a temperature of about 20 to 60° C. and a total pressure of 30 to 50 bara in the presence of a catalyst selected from Raney nickel, Raney cobalt and supported catalysts comprising nickel or cobalt deposited on a catalyst support material. This embodiment of the invention usually gives selectivity of CPCA to CPMA 92 to 98% based on a total conversion of CPCA (to other compounds) of 98 to 100%.

The process may be carried out in a continuous, semi-continuous or batch mode of operation. For example, in continuous operation CPCA and ammonia may be introduced into a mixing zone wherein the imine is formed from the reaction of CPCA and ammonia. The imine ithen is passed over a fixed bed of a supported nickel or cobalt catalyst wherein the imine is hydrogenated in the gas phase or, preferably, the liquid phase, optionally in the presence of a diluent or solvent.

The processes provided by the present invention are further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic spectrometry and gas chromatography-mass spectrometry by comparison to authentic samples. The percentages specified in the examples are by weight unless otherwise specified.

EXAMPLE 1

To a 300-mL autoclave was charged water-wet Raney nickel (5 g) and CPCA (70 g, 99% pure). The autoclave was purged twice with nitrogen. Ammonia (68 g) was charged to the autoclave while maintaining the temperature below 50° C. The mixture was stirred at 50° C. for 3 hours then pressurized with hydrogen to 42.5 bara. The mixture was stirred under these conditions until no more hydrogen was absorbed (10 hours). After cooling to room temperature and venting, the catalyst was filtered off. Analysis of the crude product showed that 98.6% of the CPCA had been converted to other compounds with a 95% selectivity to CPMA in 94% yield.

EXAMPLE 2

To a 19-liter autoclave was charged water wet Raney nickel (315 g) and CPCA (4410 g, 93% pure, contains 6% crotonaldehyde). The autoclave was purged twice with nitrogen and then ammonia (4284 g) was charged to the autoclave while maintaining the temperature below 50° C. The mixture was stirred at 50° C. for 3 hours and hydrogen was fed to the autoclave to a total pressure of 42.5 bara. The mixture was stirred under these conditions until no more hydrogen uptake occurred (16 hours). After cooling to room temperature the catalyst was separated from the crude, liquid product by filtration to give 5699.2 g of crude product. The crude product consisted of 69.14% CPMA representing 3940.4 g CPMA (95% yield). No CPCA was detected (100% conversion). Distillation through a 1.22 meter (4 feet) column containing Penn State packing and 3:1 reflux ratio gave a 95% recovery of CPMA having a purity of greater than 98%.

EXAMPLE 3

To a 300-mL autoclave was charged water-wet Raney cobalt (5 g) and CPCA (70 g, 99% purity). The autoclave was purged twice with nitrogen and then ammonia (68 g) was charged to the autoclave while maintaining the temperature below 50° C. The mixture was stirred at 50° C. for 3 hours and then pressurized with hydrogen to 42.5 bara. The mixture was stirred under these conditions until hydrogen uptake ceased (10 hours). After cooling to room temperature and venting, the catalyst was filtered off. Analysis of the crude product showed that 100% of the CPCA had been converted to other products with a 92% selectivity to the formation of CPMA.

EXAMPLE 4

To a 300-mL autoclave equipped with a catalyst basket containing 10 g of a supported nickel catalyst was placed CPCA (70 g, 99% purity). The catalyst consisted of 57 weight percent nickel on an alumina support and was pretreated with hydrogen at 200° C. prior to its use in this example. The autoclave was purged twice with nitrogen and then ammonia (68 g) was charged to the autoclave while keeping the temperature below 50° C. The mixture was stirred at 50° C. for 3 hours and then the autoclave was pressurized with hydrogen to 42.5 bara. The mixture was stirred under these conditions until no more hydrogen uptake occurred (16 hours). After cooling to room temperature and venting, the catalyst was removed. Analysis of the crude product showed that 98% of the CPCA had been converted to other compounds with a 93% selectivity to the formation of CPMA.

EXAMPLE 5

To a 250-mL pressure bottle were charged 4 g water-wet Raney nickel catalyst and CPCA (10 g, 92% purity) followed by 28% aqueous ammonia solution (50 g). The bottle was sealed in a Parr shaker and shook for 30 minutes, then pressurized with hydrogen to 4.8 bara and shook for 15 hours (until no further hydrogen uptake occurred). The mixture was maintained at 25 to 28° C. throughout the reaction period. After venting and the removal of the catalyst, GC analysis showed that the crude product comprised 81.5% CPMA (disregarding the water).

EXAMPLE 6

To a 250-mL pressure bottle were charged 7 g water-wet Raney nickel catalyst and CPCA (37 g, 90% purity) followed by 28% aqueous ammonia solution (30.4 g). The bottle was sealed in a Parr shaker and shook for 30 minutes, then pressurized with hydrogen to 5 bars absolute and shook for 40 hours (until no further hydrogen uptake occurred). The mixture was maintained at 25 to 28° C. throughout the reaction period. After venting, the crude product was purified by distillation to give 25.23 g of CPMA in 75%-isolated yield.

COMPARATIVE EXAMPLE 1

To a 300-ml autoclave was charged with CPCA (35 g, 93% purity, contains 6% crotonaldehyde) and a supported platinum catalyst containing 5% Pt of carbon (4 g). The autoclave was purged with nitrogen gas twice to exclude air and then was charged with ammonia (34 g) followed by hydrogen to a pressure of 12.5 bara. The autoclave was maintained at 45° C. for 5 hours. After cooling to room temperature and venting, GC analysis showed 82% of CPCA had been converted to over alkylation products and ring cleavage products with higher boiling points. There was no CPMA produced.

COMPARATIVE EXAMPLE 2

To a 300-mL autoclave was charged a supported platinum catalyst containing 5% Pt on carbon (5 g) and CPCA (70 g, 99% pure). The autoclave was purged twice with nitrogen. Ammonia (68 g) was charged to the autoclave while keeping the temperature below 50° C. The mixture was stirred at 50° C. for 3 hours then pressurized with hydrogen to 42.5 bars. The mixture was stirred under these conditions until no more hydrogen uptake occurred (10 hours). After cooling to room temperature and venting, the catalyst was filtered off. Analysis of the crude product showed that 83.64% of the CPCA had been converted to other products but that no CPMA had been produced.

The invention has been described in detail with particular reference to preferred embodiments thereof, but it will be understood that variations and modifications can be effected within the spirit and scope of the invention.

I claim:

1. Process for the preparation of cyclopropanemethylamine (CPMA) which comprises the steps of (1) contacting cyclopropanecarboxaldehyde (CPCA) with ammonia in a reaction zone to produce an imine compound having the structure CP—CH=NH wherein CP is cyclopropyl and (2) contacting the imine compound with hydrogen at a temperature of about 10 to 150° C. and a hydrogen pressure of about 1 to 415 bar absolute (bara) in the presence of a nickel or cobalt catalyst.

2. Process according to claim 1 wherein step (1) is carried out at a temperature of about −5 to 150° C. using 1 to 100 moles ammonia per mole CPCA.

3. Process according to claim 1 which comprises the steps of (1) contacting CPCA with ammonia at a temperature of about 20 to 50° C. to produce an imine compound having the structure CP—CH=NH wherein CP is cyclopropyl and wherein the amounts of CPCA and ammonia fed to the reaction zone give an ammonia:CPCA mole ratio of about 2:1 to 6:1 and (2) contacting the imine compound with hydrogen at a temperature of about 20 to 80° C. and a total pressure of about 1.4 to 70 bara in the presence of a nickel or cobalt catalyst selected from Raney nickel, Raney cobalt, and supported nickel and cobalt catalysts.

4. Process for the preparation of cyclopropanemethylamine (CPMA) in a single pressure vessel by the steps consisting essentially of (1) contacting cyclopropanecarboxaldehyde (CPCA) with ammonia at a temperature of 20 to 50° C. and a pressure in the range of ambient to about 22 bara in the pressure vessel using an ammonia:CPCA mole ratio of about 3:1 to 4:1 to produce an imine compound having the structure CP—CH=NH wherein CP is cyclopropyl and (2) contacting the reaction mixture resulting from step (1) with hydrogen at a temperature of about 20 to 60° C. and a hydrogen pressure of about 30 to 50 bar absolute in the presence of a catalyst selected from Raney nickel, Raney cobalt and supported catalysts comprising nickel or cobalt deposited on a catalyst support material.

5. Process according to claim 4 wherein the catalyst is Raney nickel, Raney cobalt, or a supported catalyst consisting of 40 to 60 weight percent nickel on alumina.

* * * * *